(12) United States Patent
Gamble et al.

(10) Patent No.: US 6,734,963 B2
(45) Date of Patent: May 11, 2004

(54) DEVELOPMENT OF A COMPACT RAMAN SPECTROMETER FOR DETECTING PRODUCT INTERFACES IN A FLOW PATH

(75) Inventors: Heather A. Gamble, Concord (CA); John C. Robbins, Concord (CA); Gervase I. Mackay, Concord (CA); Harold I. Schiff, Concord (CA)

(73) Assignee: Unisearch Associates Inc., Concord (CA)

( * ) Notice: Subject to any disclaimer, the term of this patent is extended or adjusted under 35 U.S.C. 154(b) by 0 days.

(21) Appl. No.: 10/051,305

(22) Filed: Jan. 22, 2002

(65) Prior Publication Data

US 2002/0113961 A1 Aug. 22, 2002

Related U.S. Application Data

(60) Provisional application No. 60/262,639, filed on Jan. 22, 2001.

(51) Int. Cl.[7] .............................. G01J 3/44; G01N 21/65
(52) U.S. Cl. ..................... 356/301; 356/318; 356/73; 250/458.1
(58) Field of Search .......................... 356/73, 301, 318; 250/458.1, 459.1, 461.1, 461.2

(56) References Cited

U.S. PATENT DOCUMENTS

| 4,620,284 A | 10/1986 | Schnell et al. |
| 5,139,334 A | 8/1992 | Clarke |
| 5,182,940 A | 2/1993 | Bailey et al. |
| 5,461,236 A | 10/1995 | Gram et al. |
| 5,596,196 A | 1/1997 | Cooper et al. |
| 5,742,064 A | 4/1998 | Infante |
| 5,751,415 A | 5/1998 | Smith et al. |
| 5,781,284 A | 7/1998 | Infante |
| 6,028,667 A | 2/2000 | Smith et al. |
| 6,100,975 A | 8/2000 | Smith et al. |

Primary Examiner—F. L. Evans
(74) Attorney, Agent, or Firm—Bereskin & Parr

(57) ABSTRACT

The present invention relates to a method and apparatus for detecting transitions between different gas or liquid products in a flow path and, more particularly, it relates to an apparatus and method utilizing Raman spectroscopy for detecting transitions between petroleum products. A Raman spectrometer is preferably to produce a monochromatic excitation beam at a wavelength of approximately 670 nm. The spectrometer consists of an entrance slit, a combined diffraction grating/focussing element, and an exit slit. The Raman signal, which exits the spectrometer exit slit is detected by a highly sensitive photomultiplier tube, and sent to a computer device for data acquisition and analysis. The proposed invention detects liquid or gas products in a flow path by detecting the changes in the composition of various petroleum products flowing through a gasoline pipeline, by means of exposing samples of various petroleum products to the Raman spectrometer system.

41 Claims, 9 Drawing Sheets

DEVELOPMENT OF A COMPACT RAMAN SPECTROMETER FOR DETECTING PRODUCT INTERFACES IN A FLOW PATH

FIELD OF THE INVENTION

The present invention relates to a method and apparatus for detecting transitions between different gas or liquid products in a flow path and, more particularly, it relates to an apparatus and method utilizing Raman spectroscopy for detecting transitions between petroleum products.

BACKGROUND OF THE INVENTION

Before the advent of lasers, the use of Raman spectroscopy as a routine analytical technique was limited due to the small number of available sources of intense, monochromatic radiation Since the 1960's, laser have become the excitation source of choice for Raman spectroscopy, as they provide much greater intensities and narrower line widths than the mercury arc lamps commonly employed previously. Furthermore, much weaker Raman signals became observable, resolution improved, which lead to laser Raman spectroscopy becoming an important benchtop tool for identifying molecular species via characteristic or "fingerprint" vibrational features. In the past, due to the special requirements of the lasers, (high voltages, cooling water, specialised personnel and space requirements), these systems tended to be large and expensive, and needed to be used in dedicated facilities.

Since then, diode lasers have become much simpler to operate. Diode lasers are small and inexpensive, can run off very low voltages (15 V or less), generate less heat, and have high conversion efficiencies compared to traditional laser Raman sources. In spite of these advantages, certain inherent properties of diode lasers have made them less appealing for use in Raman spectroscopy. These include lower intensities, a less monochromatic output ("mode hopping"), greater beam divergence, and excitation wavelengths restricted to the near to mid-IR regions. With recent advances in diode laser technology, many of these difficulties have been overcome, and Raman spectrometers with diode lasers as the excitation source have begun to appear.

One big advantage of using diode lasers as a source for Raman spectroscopy was to move the technique out of the lab and into the realm of field measurements and process monitoring. Relatively high molecular weight organics, such as petroleum products, various plastics, and types of edible oils have been differentiated on the basis of their Raman spectra generated using a portable diode laser based Raman instrument. These compounds are good candidates for Raman based analysis due to the presence of strong Raman features with shifts in the region of 700–1700 $cm^{-1}$. Raman analysis of commercial grade gasoline in particular can benefit from an excitation source in the near to mid-IR, to avoid interference from background fluorescences which can be excited at lower wavelengths. These fluorescence signals depend on the excitation wavelength, and can be so strong that they completely obscure the Raman features which would otherwise appear.

A number of studies have used Raman spectroscopy to examine fuels or mock fuel mixtures. These include a quantitative analysis of xylene isomers in mock petroleum fuels using a diode laser Raman spectrometer with an excitation wavelength of 800 nm. A partial least squares regression analysis routine was used to correlate the individual xylene isomer concentrations to the Raman signal, without the use of an internal standard. For samples containing between 1.5 and 15% xylenes, the concentrations were determined to within ±0.1% for the meta- and para-isomers, and to within ±0.15% for ortho-xylene. Other studies include a comparison of near-IR and Raman spectroscopies for the determination of the chemical and physical properties of naptha, an analysis of aviation turbine fuel composition, and a system designed to correlate the Raman spectra of gasolines with their octane ratings. The first three studies were all laboratory based, while the fourth describes a partial least squares regression analysis routine which was applied to spectra recorded on a commercial FT-Raman spectrometer with a Nd:YAG source. A large "training set" of spectra taken from fuels with known octane ratings was used to build a model to predict the octane rating of fuels not included in the training set. The accuracy of the determined octane ratings depended on the accuracy of the training set used to create the model. In general, a given fuel octane rating can correspond to any number of different chemical "recipes", i.e. the octane rating does not uniquely define the exact chemical composition of the fuel. Gasoline derived from a common source, or processed by a particular refinery, may show a particular pattern, which the training set can "learn" to recognize. However, a fuel derived from a different source may not match the defined pattern, necessitating the acquisition and use of a new training set.

The problem of measuring the octane rating of a given fuel, other than by the empirical "engine knock" tests used to define the quality, is clearly not straightforward. The training set approach does have its uses. However, it relies on being able to establish a reliable base (the training set), and can get somewhat cumbersome when applied to a large, widely varying set of samples. The problem of distinguishing between various grades of gasoline, without attempting to specify an octane rating, is significantly less demanding. It is also still extremely important. When the finished products leave the refinery, they travel through pipelines to distribution stations, where they are directed into holding tanks before being transported by truck to local filling stations. Any or all of the different grades of gasoline or distillates may pass sequentially through a given section of pipe. It is thus important to be able to determine exactly when one product lot ends, and the next begins.

Various techniques have been used to identify the exact product interface in such a setting. As a basic requirement, one needs a measurable physical or chemical property, which differs not only from product to product, but from grade to grade. Ideally, the measurements should be fast, non-destructive, able to be made in-situ, give a clearly visible (large) change when an interface occurs, and produce an output, which does not require a high degree of technical skill to interpret.

One technique is to measure the density of the products as they flow past a particular point near the outlet into the holding tanks. The density measured at this point in actually based on a sonometer, which measures the speed of sound as it passes through the sample. This technique produces large changes at gasoline to distillate interfaces, but can have trouble distinguishing between grades of gasoline, and between diesel vs. low sulphur diesel oils. Viscosity or colour changes have also been used. Another device, advertised commercially, detects interfaces by measuring the electrical resistivity of the product as it flows past a point.

The abundance of techniques available serves to demonstrate the importance of detecting product interfaces in a gasoline pipeline. Accordingly, there is a need for a method, which reliably and accurately detects product interfaces in a pipeline in real-time. Particularly, there is need for a method and apparatus which can accurately and reliably detect product interface between a wide range of petroleum products, such as gasoline products as well as other distillates (diesel, jet fuel, etc.).

SUMMARY OF THE INVENTION

In accordance with the present invention a compact, portable Raman spectrometer system suitable for in situ use in hostile environments has been proposed. The source is a high power (500 mW), broad band red diode laser which has been mode locked using an external cavity. This produces a monochromatic excitation beam at a wavelength of approximately 670 nm. The spectrometer consists of an entrance slit, a combined diffraction grating/focussing element, and an exit slit. The resolution of the Raman spectra obtained is excellent (7.2 cm$^{-1}$ FWHM at a Raman shift of 1000 cm$^{-1}$). The Raman signal, which exits the spectrometer exit slit is detected by a highly sensitive photomultiplier tube (PMT), and sent to a computer device (PC-104) for data acquisition and analysis.

The proposed invention described herein detects liquid or gas products in a flow path. Specifically, this invention detects changes in the composition of various petroleum products flowing through a gasoline pipeline, by means of exposing samples of various petroleum products to the Raman spectrometer system. The petroleum products of interest consisted of four distillates (diesel oil, low sulphur diesel, jet fuel, and furnace oil), and three different grades of gasoline (regular unleaded, premium 91, and premium US92). Both the hardware and software is tailored specifically to suit this application. A computer acquires full Raman spectra from the Raman spectrometer system, wherein data obtained from the spectra is processed using a multiple-dimension "least squares" routine.

BRIEF DESCRIPTION OF THE DRAWINGS

For a better understanding of the present invention and to show more clearly how it may be carried into effect, reference will now be made, by way of example, to the accompanying drawings:

FIG. 1b illustrates a schematic representation of a mirror arrangement used in collaboration with the cell illustrated in FIG. 1a;

DETAILED DESCRIPTION OF THE INVENTION

Figure 1A:
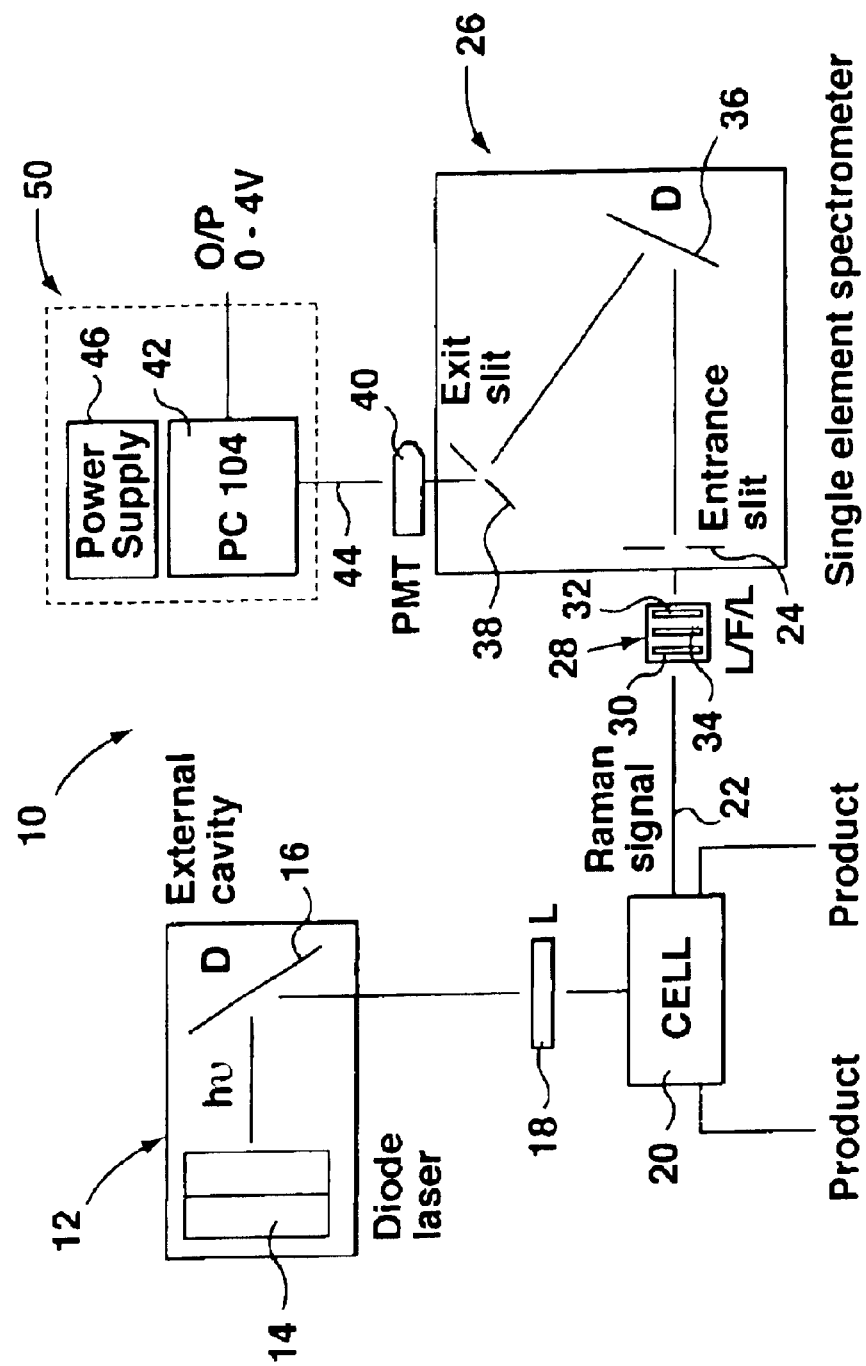
FIG. 1a illustrates a schematic representation of a Raman spectrometer system.

FIG. 1a illustrates a Raman spectrometer system 10 for detecting interfaces between various petroleum products flowing through a pipeline or a suitable conduit structure. It will also be appreciated that in accordance with the present invention, the product or material interfaces between other types of gas or liquid in a flow path can be detected. The spectrometer system 10 comprises a high power excitation source 12, which includes a high power (up to 500 mW), broad band diode laser device 14 with a central emission wavelength of 670 nm and an external cavity grating device 16. The diode laser 14 is locked into single mode operation by means of the external cavity 16, wherein the external cavity 16 provides frequency-selective optical feedback. The diode laser 14 and external cavity 16 are operated to form a mod-locked external cavity laser that emits monochromatic red light with a spectral resolution (FWHM linewidth) of 0.2 nm. The diode laser 14 also includes a thermoelectric cooling element (not shown in FIG. 1a), a heat sink and fan, which provides a means for maintaining wavelength stability and device integrity (avoiding device destruction). The single mode output intensity is greater than or equal to the output from the laser whilst in multimode operation when the laser is running at up to 67% capacity (as measured by the drive current). At drive currents above 67% of capacity, the single mode output intensity is less than the intensity measured during multimode operation. In accordance with an alternative aspect of the present invention, the excitation source may incorporate any other laser device capable of generating wavelengths, which produce Raman spectra from the sample or products flowing in a carrier structure such as a pipeline. Depending on the material under analysis, it may be necessary to use different excitation wavelengths for producing Raman spectra. Consequently, different diode laser sources may be utilized.

Figure 1B:
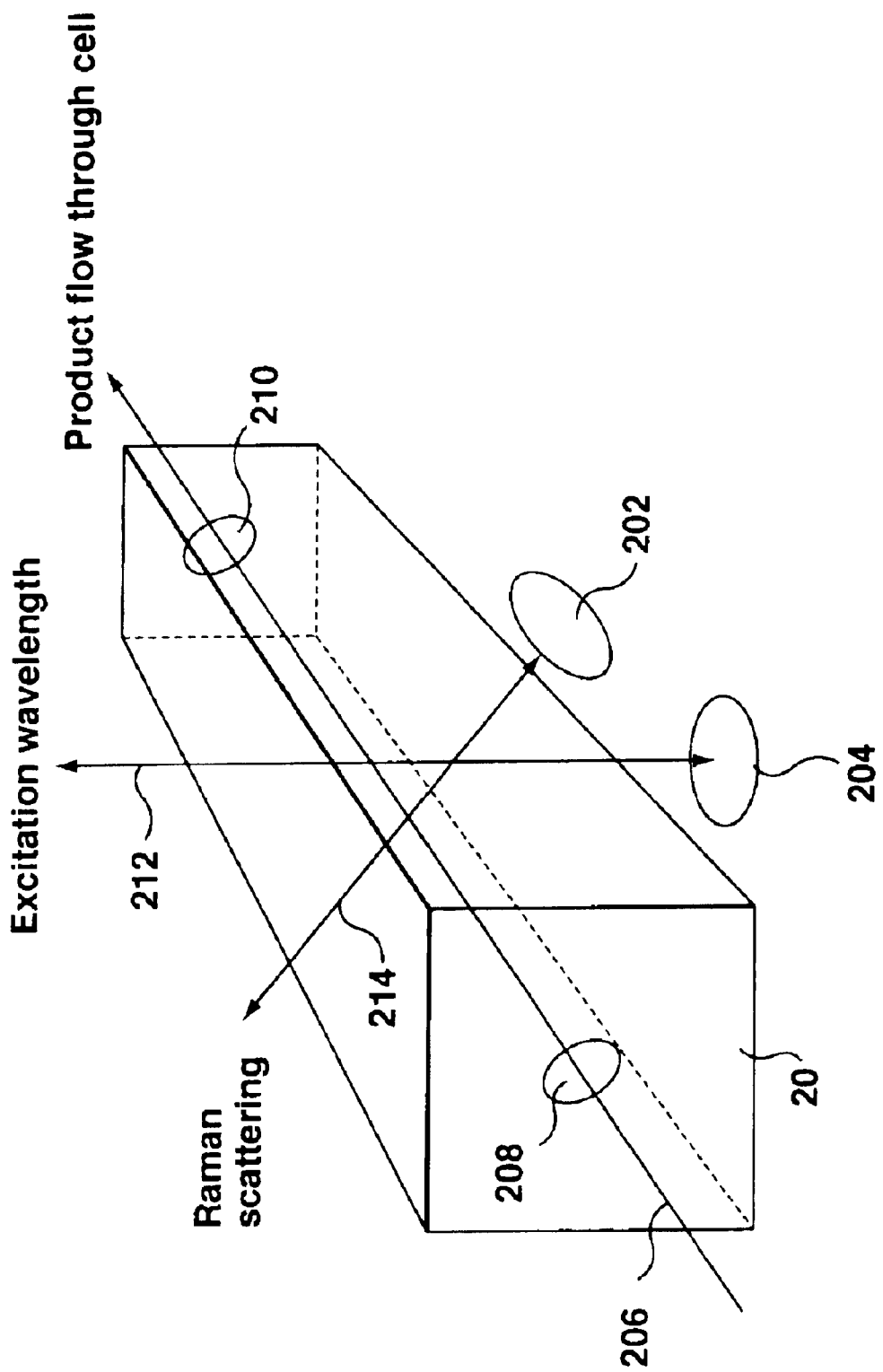

The optical light signal (red light) is emitted from the excitation source 12 and received by a lens device 18. The lens device 18 receives and focuses the light signal into the center of a high pressure, stainless steel sample cell 20. The cell 20 is equipped with four ½ inch diameter, 4.75 mm thick AR coated fused silica windows which allow the light signal (red light) to pass into and out of the cell 20. As illustrated in FIG. 1b, a pair of gold mirrors 202, 204, one below and one on the side of the cell respectively, are used to enhance the Raman signal intensity by effectively doubling the number of transitions (passes) the light signal makes through the sample. As illustrated in FIG. 1b, a product under analysis, indicated by 206, flows into the cell 20 by means of a first opening 208, and flows out of the cell 20 by means of a second opening 210. As the product flows through the cell between the first and second openings 208, 210, the light signal, as indicated by 212, from the excitation source illuminates the product, by making a first transition through the cell 20. The light signal, indicated by 212 (also referred to as an excitation wavelength) generates a Raman scattered signal, wherein a first portion of the Raman signal is output from the cell along path 214 to the spectrometer device 26 (see FIG. 1a). A second portion of the generated Raman signal is received by the first mirror 202 and reflected back along path 214 to the spectrometer device 26 (see FIG. 1a). Consequently, the first mirror redirects any generated Raman signal propagating away from the spectrometer device 26 back towards the spectrometer device 26, which increases the received Raman signal intensity. The second mirror 204 reflects the light signal, indicated by 212, which passes through the flowing product in the cell, back through the flowing product. Hence, by doubling the number of transitions the light signal, indicated by 212, makes through the cell, the intensity of the generated Raman scattered signal is increased. FIG. 1a illustrates the generated Raman scattering signal output from the cell, as indicated by 22. The sample (product) flows continuously through the cell 20, which was pressure tested to 2000 psi.

As illustrated in FIG. 1a, the Raman signal, indicated by 22, is emitted from the cell 20 and focussed onto an entrance slit 24 of a spectrometer 26 by means of a lens/filter assembly 28. The lens/filter assembly 28 comprises an optical filter 34, an input coupling lens 30 and an output coupling lens 32. The lens/filter assembly 28, removes any residual optical signals from the Raman signal (90% optical transmission above 680 nm), which includes the 670 nm light signal (red light) emitted from the excitation source 12. The Raman signal 22 is coupled by the lens/filter assembly 28 to the entrance slit 24, where it is diffracted by a concave diffraction grating 36 within the spectrometer 26. The concave diffraction grating 36 directs the Raman signal onto the spectrometer's exit slit 38, wherein the exit slit 38 couples the Raman signal to an optical detection device 40 such as a photomultiplier tube (PMT). The Raman signal is detected by a photomultiplier tube 40 and sent to a computer device 42 for processing. A limited rotation electromagnetic drive (not shown in FIG. 1a) repetitively turns the concave grating 36 through a small angle under precise servo control. Turning the grating 36 (one rotation or single scan) under servo control provides a wavelength scanning range of 25 nm, from 690–715 nm. This corresponds to Raman shifts of 700–1220 $cm^{-1}$.

The Raman spectrometer system 10 is installed in-situ on a working pipeline. In a preferred embodiment, the excitation source 12, sample cell 20, spectrometer 26, and PMI 40 are housed in a NEMA rated explosion proof box with inside dimensions of 30 cm×30 cm×15 cm. This box is mounted outdoors, adjacent to the pipeline. The product is drawn through stainless steel tubing from the main pipeline, through the sample cell, and returned to the main pipeline, providing a continuous flow through the cell. A separate control unit 50 includes both the computer 42 and a power supply 46, and is located inside a nearby monitoring station. The power supply 46 provides power to all the main components of the Raman spectrometer system 10 (e.g. computer, laser current driver, cooling fan, etc.). A conductor medium 44 such as a 20 m length of single shielded co-axial cable transmits the Raman signal from the optical detection device 40 (photomultiplier tube) to the computer 42 inside the control unit 50. Once the computer 42 processes the received Raman signal, an indication signal consisting of a single voltage value sealed between 0 and 4 V is sent from the back of the control unit 50 to the end user. A change in the output voltage indicates a change in the product flowing through the cell. More detailed data is also logged and stored on the computer 42, and can be accessed for diagnostic purposes by including a computer monitor and keyboard within the control unit 50.

The raw data based on the received Raman signal 22 is sent to the computer 42. This data consists of a continuous series of scans (25 nm range), each containing information capable of generating a Raman spectrum of optical intensity (response of the PMT optical detection device) as a function of wavelength (angle of the diffraction grating). In accordance with the present invention, the data is averaged for approximately 90 s (100 scans).

The resulting incoming spectrum contains features which are representative of the composition of the product which is flowing through the cell. In accordance with the present invention, a carefully constructed product differentiation algorithm is used to assign a signal value (an output voltage) based on the appearance of the incoming spectrum, and/or the extent to which the incoming spectrum resembles previous incoming spectra. Consequently, the algorithm analyses the data corresponding to the averaged Raman scans, and determines the interface between different products flowing through the cell. In accordance with the present invention, the interface between petroleum products are determined, whereby the algorithm relies upon certain properties of refined petroleum products, which have been established empirically in the laboratory during the development of the Raman spectrometer system 10. These properties are fairly basic, and are expected to be widely applicable for most refined petroleum products world-wide. It will also be appreciated that this algorithm may be extended to analysing any substance that provides a good Raman signal, The Raman spectra of all grades of gasoline are dominated at Raman shifts between 700 and 1200 $cm^{-1}$ by features which can be attributed to a small group of compounds such as: Toluene, ortho-, meta-, and para-xylenes, Iso-octane, cyclohexane, and alkyl-cyclohexanes. Different grades of gasoline contain varying proportions of these compounds. For example, the toluene feature produces a Raman shift of 1001 $cm^{-1}$, and is always the most prominent. There is no universal relationship, which reliably correlates simple ratios of any of these species to the octane rating of a given product.

Any Raman features in spectra obtained from distillates such as diesel, low sulphur diesel, or furnace oil are obscured by a huge fluorescent signal. The relative strengths of the fluorescence signals from the different distillates were distinct and reproducible. Jet fuel fluoresced only weakly, but still showed little in the way of Raman features. Linear alkanes, which have very weak, broad Raman features between 700 and 1200 $cm^{-1}$, are present in greater abundance in distillates, including jet fuel. Aromatics and cyclic or branched alkanes, which have strong Raman features, are undesirable in diesel fuels Occasional gasoline samples fluoresced weakly as they flowed through the pipeline, but not to the extent of completely obscuring the Raman features.

Figure 2:
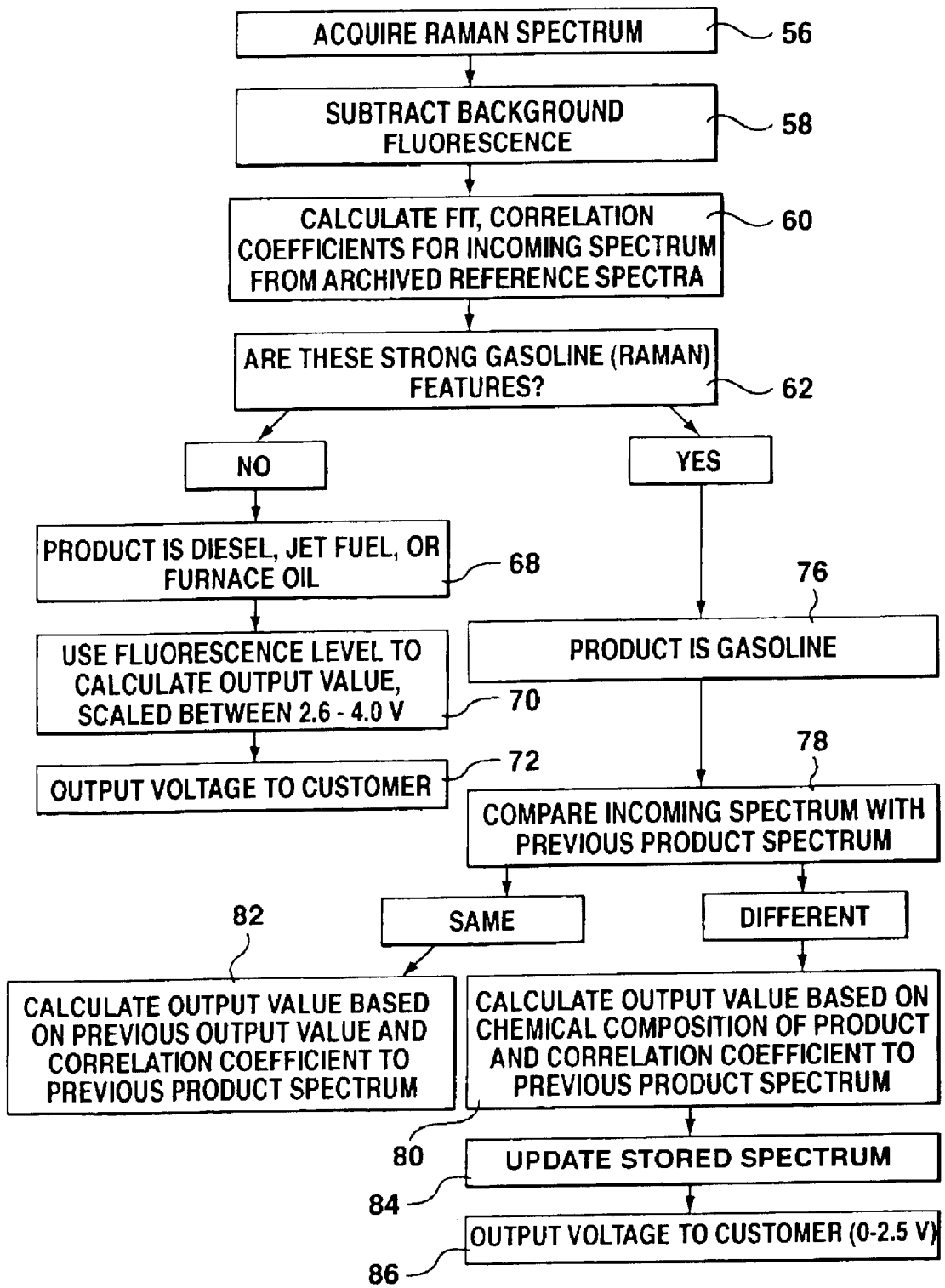
FIG. 2 illustrates a flow chart representation of a product differentiation algorithm used in determining product interfaces.

On the basis of these observations, the product differentiation algorithm was constructed along two paths. A flowchart mapping the decision making process is shown in FIG. 2.

Along the first path, strongly fluorescent products were assigned an output voltage in the range of 2.6–4.0 V. For the purpose of this disclosure, the exact value is calculated based on the intensity of the fluorescence of the current sample, according to Equation [1]. For example, weakly fluorescent jet fuel will have a very small value for F, and will produce an output value close to 2.6. Furnace oil, which can fluoresce so strongly the signal goes off scale, will have a value close to 4.0. The value of F in Equation [1] is constrained to a maximum of $F_{max}$=2.0. Intermediate fluorescence levels, associated with diesel or low sulphur diesel, give intermediate (but distinct) output values.

$$V=2.6+F*1.4/F_{max} \quad [1]$$

V value output to customer

F ratio of fluorescence levels of incoming to stored reference spectra $F_{max}$ maximum fluorescence ratio before signal goes off scale It will be appreciated that a more detailed analysis of the incoming data is required to differentiate between gasoline products For this reason, the algorithm must first determine whether the incoming product is gasoline or other distillates. Referring to FIG. 2, in a step 56, the computer receives raw data corresponding to an acquired Raman spectrum (averaged spectrum based on the 90 s scan time). Following this data acquisition process, in a step 58, the background fluorescence is subtracted from the acquired Raman spectrum data. In a step 60, a series of multi-dimensional least square calculations are carried out in order to fit the received incoming spectrum data to a set of data corresponding to the reference spectra already stored in the computer 42 (FIG. 1a). The data corresponding to the reference spectra are used in determining whether gasoline is being analyzed or other distillate products such as diesel, low sulphur diesel, jet fuel or furnace oil. The stored spectra (six) data are reference spectra of pure compounds, which were found to be important components of gasoline products. The stored reference spectra (data) are pure toluene, meta-xylene, iso-octane, cyclohexane, and methylcyclohexane (five pure compounds), which were acquired in the laboratory and stored on the computer 42 (PC-104). Also, a sixth reference spectrum (data) was added, which includes a characteristic curve from a strongly fluorescent compound. In the step 60, data for each incoming spectrum is fit to the data corresponding to the mentioned reference spectra using a multi-dimensional least squares fit routine. The incoming product spectrum (data) is compared channel by channel (x values: Raman shift ($cm^{-1}$) value) with a hypothetical "test" spectrum (data) which is a composite of the six mentioned reference spectra (data). This test spectrum data is built by applying a multiplier to each reference spectrum, then taking the sum. The six multipliers are adjusted to minimize the difference between the incoming product spectrum (data) and this "test" or composite spectrum (data). The set of multipliers which minimizes the difference makes up a set of six optimized fit coefficients, one for each reference spectrum. The routine also calculates an individual correlation coefficient for each individual reference spectrum (data points) with respect to the incoming product spectrum (data points). In the case where the incoming product contains substantial proportions of all or many of the individual compounds used to create the reference set, then none of these individual correlation coefficients will be especially close to one (i.e. the shape of the incoming product spectrum will not strongly resemble the shape of any individual reference spectrum). Hence, for each incoming spectrum, this routine generates a set of six fit coefficients (the multipliers) and six individual correlation coefficients (a measure of the degree to which the incoming spectrum resembles a given reference spectrum), one pair for each stored reference spectrum.

The routine also calculates a total correlation coefficient for the incoming product spectrum (data) with respect to the optimized "test" or composite spectrum (data). If the product consists entirely or almost entirely of compounds, which are included in the six reference spectra, the multi dimensional correlation coefficient will be very close to one. This total correlation coefficient gives a measure of how well the incoming spectrum data matches the composite reference spectrum data and used for diagnostic monitoring purposes.

Based on the values of these individual correlation coefficients, in a step 62, the algorithm tests for the presence of strong Raman features in the incoming data. If no Raman features are found, the output value is calculated based on the fluorescence. In this case, the algorithm moves to a step 68, wherein the product it determined to be diesel, jet fuel or furnace oil. If strong Raman features are present, the algorithm moves to a step 76, wherein the product is assumed to be gasoline.

Subsequent steps 78, 80, 84, and 86 are for processing and detecting interfaces between varying grades of gasoline. In a step 78, data corresponding to the incoming spectrum is compared with data corresponding to a spectrum, which is representative of the product flowing a few minutes previously, This previous product spectrum (data) is stored on the PC-104 computer as a temporary or "moving" reference spectrum (data). It is updated every time the incoming spectrum is determined to contain strong Raman features (i.e. for every incoming spectrum, which indicates gasoline). In the step 78, the comparison between the incoming spectrum data and the moving reference spectrum data is performed using a single dimension least squares fit. The algorithm looks at the data corresponding to each spectrum (incoming spectrum and moving reference spectrum) point by point and compares the two. The difference between the corresponding signal intensities (the "y" values) for each channel number (the "x" values) can be quite large depending on how alike or unalike, with respect to both shape and signal intensity, the two spectra are. A constant multiplier is then applied to the stored "moving" reference spectrum data (i.e. multiplying all the "y" values corresponding to the stored moving spectrum data by a given value). The multiplier that minimizes the difference between the corresponding signal intensities (y values) is the (best) fit coefficient. The correlation coefficient, normally denoted $R_{pp}$, gives a measure of how good this fits is (i.e. how similar in shape the two spectra are). A perfect fit has a correlation coefficient of exactly one. Consequently, a fit coefficient and correlation coefficients are generated, which characterize the degree of similarity between the current, incoming spectrum, and the stored moving reference spectrum (the previous product spectrum). If the correlation coefficient is above a defined cut-off, the product is deemed to be the same (no interface). In this case, in a step 82, the output value is calculated according to equation [2a]. For this case, the output value is calculated from a previously calculated "moving" constant $C_M$ defined by equation [3] and the (small) difference between the incoming and previous product spectra (correlation coefficient).

$$V=C_M+1.0+5*(1-R_{pp}) \text{ (if } C_M \text{ is unchanged or has increased)} \quad [2a]$$

$$V=C_M+1.0-5*(1-R_{pp}) \text{ (if } C_M \text{ is decreased)} \quad [2b]$$

V value output to customer $C_M$ moving constant $R_{pp}$ correlation coefficient of incoming to previous product spectrum The third term is constrained to a maximum value of 0.5 to prevent V from going out of range.

If the correlation coefficient is below the defined cut-off, this is taken to indicate a clear difference between the current and previous product spectra (an interface). In this case, in a step 80, the moving constant is re-assigned based on the chemical composition of the current incoming product according to Equation [3].

$$C_M=A*(R_{tol}+R_{m-xylene})-B*R_{iso-C8} \quad [3]$$

$C_M$ moving constant

A, B empirically derived constants $R_{tol}$ correlation coefficient of incoming spectrum to stored toluene reference spectrum $R_{m\text{-}xylene}$ correlation coefficient of incoming spectrum to stored meta-xylene reference spectrum $R_{iso\text{-}C8}$ correlation coefficient of incoming spectrum to stored iso-octane reference spectrum In other embodiments of the present invention, whereby a product other than petroleum is being analyzed, the equations ([1], [2] and [3]) which are used to determine the product interface will vary in accordance with the type of product or compound under analysis. For example, in accordance with the present invention, the correlation coefficients defined in equation [3] relate to the particular incoming product (i.e. gasoline) being analyzed. If another product is flowing through the sample cell, the correlation coefficients, will be based on other specific compounds stored as reference spectra in the computer. In the present embodiment, the correlation coefficients are based on the compounds found in gasoline, such as iso-octane, meta-xylene, and toluene.

The constants A and B are empirically derived, and are used to scale the moving constant to give values between −0.5 and 1.0 for a wide range of gasoline samples. Once the moving constant has been updated, the output value is calculated using Equation [2a] or [2b] based on whether the recently calculated value of $C_M$ is higher or lower than the previous $C_M$ value. If it is higher, then $C_M$ is substituted within equation [2a], and if lower, then $C_M$ is substituted within equation [2b]. In a step 84, the stored spectrum is updated, whereby the present incoming spectrum data becomes the new moving reference spectrum (data). In a step 86, based on the different grade of gasoline detected at the interface, an output voltage between 0–2.5 V is provided to the end user or customer (i.e. the output of equation [3]). The steps illustrated in FIG. 2 and described in the previous paragraphs constantly analyze incoming products flowing in the cell.

If the product is determined to be diesel, jet fuel or furnace oil, in a step 70, the fluorescence level is calculated using equation [1]. Depending on the product, an output value between 2.6–4.0 V is generated and provided to the end user or customer, as defined by step 72. As previously discussed, each product (not gasoline) will have a relatively different fluorescence strength. Therefore, any changes in fluorescence signal strength can be correlated to determining a product interface.

The system described above produced good quality Raman data over a wavelength span of 25 nm (Raman shifts from 700–1200 $cm^{-1}$). This shift region covers an aromatic ring breathing mode which gives a strong feature at 990–1010 $cm^{-1}$ from mono-, meta- or tri-substituted benzene (important constituents of gasoline). It also covers a ring vibration mode from para substituted benzene (e.g. para-xylene, 810 and 830 $cm^{-1}$), and various modes from branched and cyclic alkanes (e.g. cyclohexane ring breathing mode at 802 $cm^{-1}$, iso-octane t-butyl symmetric stretch at 745 $cm^{-1}$).

Figure 3:
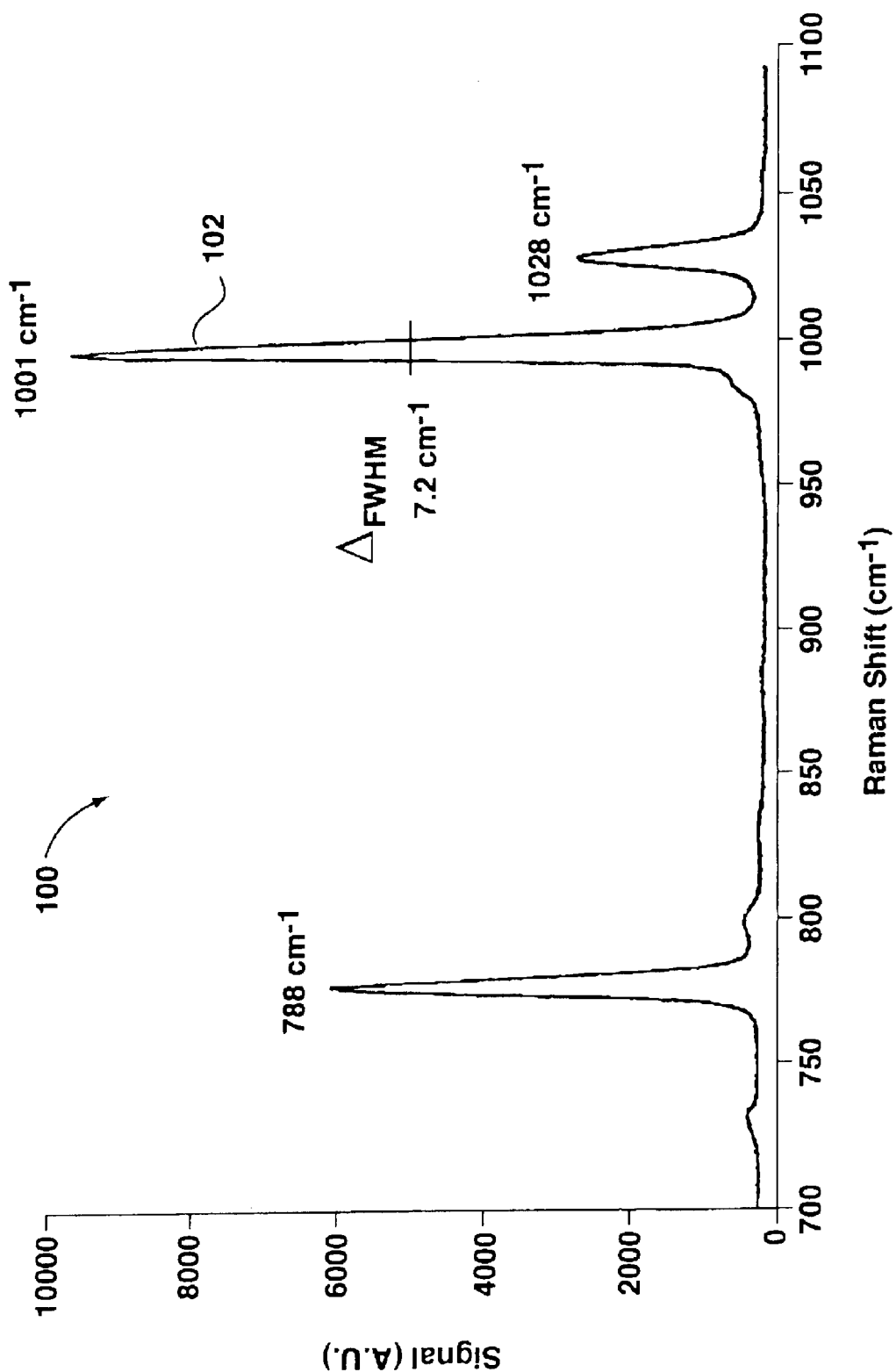
FIG. 3 illustrates a measured Raman spectrum of pure toluene obtained by the Raman spectrometer system illustrated in FIG. 1.

FIG. 3 shows a spectrum, as defined by 100, of pure toluene obtained from this system 10 (FIG. 1). The resolution is determined to be approximately 7.2 $cm^{-1}$ FWHM for the 1001 $cm^{-1}$ peak, indicated at 102. Also, the excitation wavelength generated by the excitation source 12 is 666 nm. The ring breathing mode of toluene has a particularly strong Raman signal, and has proven to be a particularly useful benchmark feature for analyzing gasoline spectra.

Refined gasoline is a mixture of hydrocarbons. Raman features from various aromatic compounds and cyclic or branched alkanes are visible in the spectra obtained from actual gasoline samples. Features from these compounds, which are important in defining the octane rating of a given fuel, are labeled in a set of gasoline spectra shown in FIG. 4. These spectra were obtained from three different grades of gasoline collected during field trials at a pipeline pumping station located in north Toronto. The strong toluene features can be observed in all three spectra, as indicated at 104, 106 and 108. The most obvious difference between the three grades of gasoline is the strength of the iso-octane peak at 745 $cm^{-1}$. Indicated at 110, which was clearest in the spectra of the premium grades of gasoline, indicated at 114 for the premium 91 grade, and at 112 for the US92 gasoline. The iso-octane peak, as indicated at 116, in the spectrum of regular unleaded gasoline, (lowest octane rating) was even loss distinct. A closer examination reveals other differences in the three spectra, visible predominantly between 700 and 775 $cm^{-1}$. For example, the meta-xylene peak at 725 $cm^{-1}$, as indicated at 120, is most prominent in the spectrum of US92 premium grade gasoline, indicated at 122, while regular unleaded fuel has stronger cyclohexane and alkyl-cyclohexane features.

Figure 4:
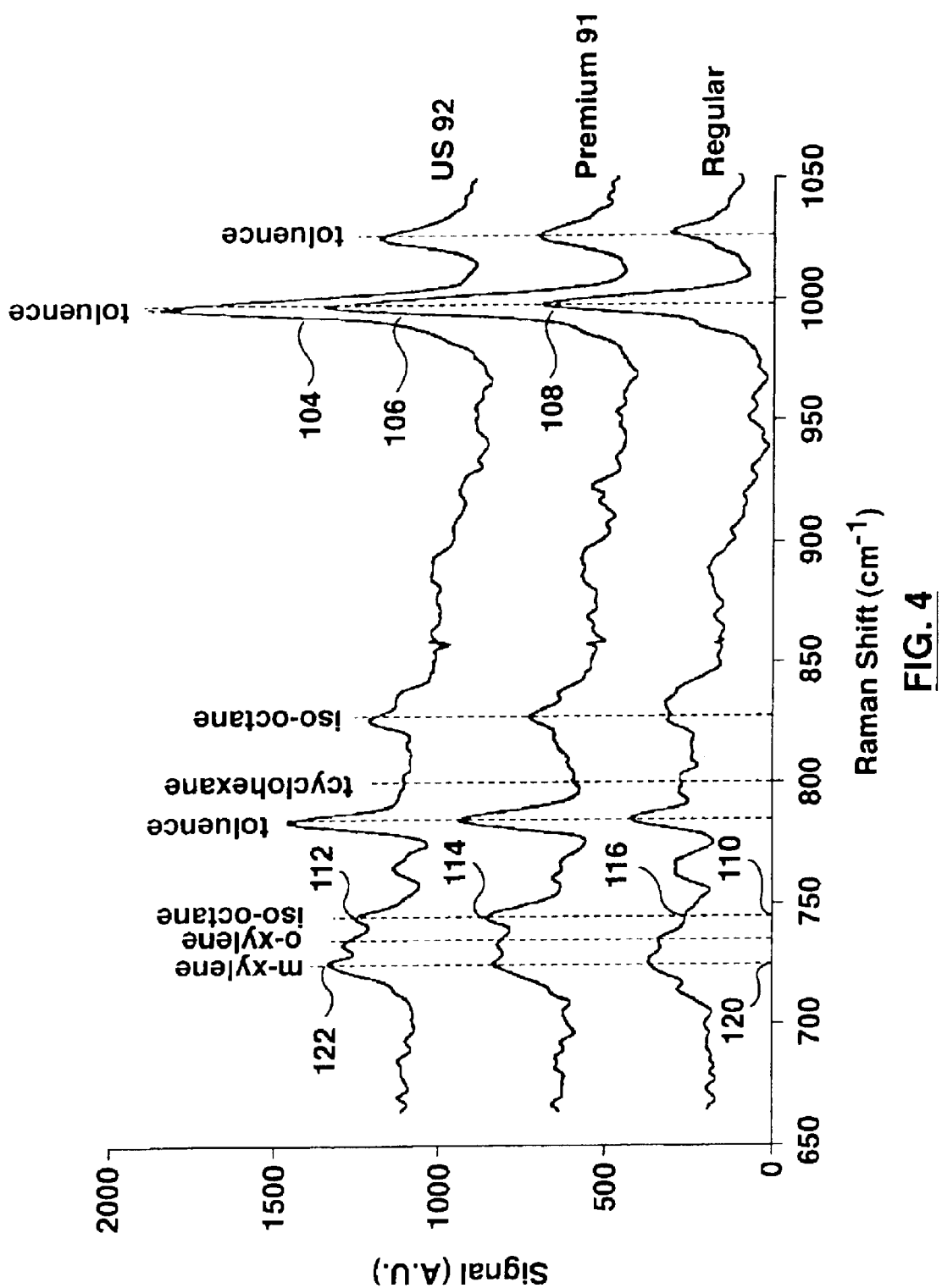
FIG. 4 illustrates a measured Raman spectrum for three grades of gasoline.

The chemical differences between regular vs. the premium grades of gasoline, as indicated by the gasoline samples illustrated in FIG. 4, appear distinguishable. Aromatics and branched alkanes such as iso octane are recognized octane enhancers. It is thus reasonable that these compounds should feature more prominently in the spectra of the premium grades. The spectra shown in FIG. 4 clearly establishes that there are differences between gasoline samples, and that these differences can be detected spectroscopically.

For the products measured over the course of two lengthy field trials, there was a tendency for the premium grades to have higher proportions of iso-octane relative to toluene than the lower (regular) grade. However, the ratios from some samples were inverted (i.e. high levels of iso-octane in some regular unleaded samples, low levels in some premium US92 fuels). Also, there are some instances in which no clear change in the iso-octane to aromatic (toluene) ratio can be observed, even when a transition is known to have occurred. As demonstrated, these "missed" transitions are not due to a lack of sensitivity in the spectrometer. Rather, they are not detected because many different compounds, not just iso-octane and toluene, affect the overall octane rating of a given fuel.

In accordance with the present invention, the end user will detect the required transitions (product interfaces) by a change in a single value (e.g. voltage), which is output as a voltage and integrated within the user's pipeline monitoring station. The noise level in the output value has to be sufficiently low relative to the magnitude of the expected changes, so that an interface could be reliably identified within one or two measurement periods.

In order to overcome the mentioned issues with detecting the gasoline transitions, the multi-dimensional least squares fitting is used. The set of six fit coefficients and correlation coefficients, which are calculated based on the corresponding six stored reference spectra, provide a quantitative basis for differentiating between gasoline samples. The magnitudes of the fit coefficients depend on the strength of the Raman signal, and thus are sensitive to external influences such as the laser intensity, or dirt particles or accumulation in the cell, which may vary over time. However, the correlation coefficients give a measure of the degree to which the incoming spectrum resembles a given reference compound, which proves to be a more reliable indicator of a product change. This is demonstrated in FIG. 5, which shows the optimized correlation coefficients of the incoming product spectrum calculated with respect to five pure compounds.

Figure 5:
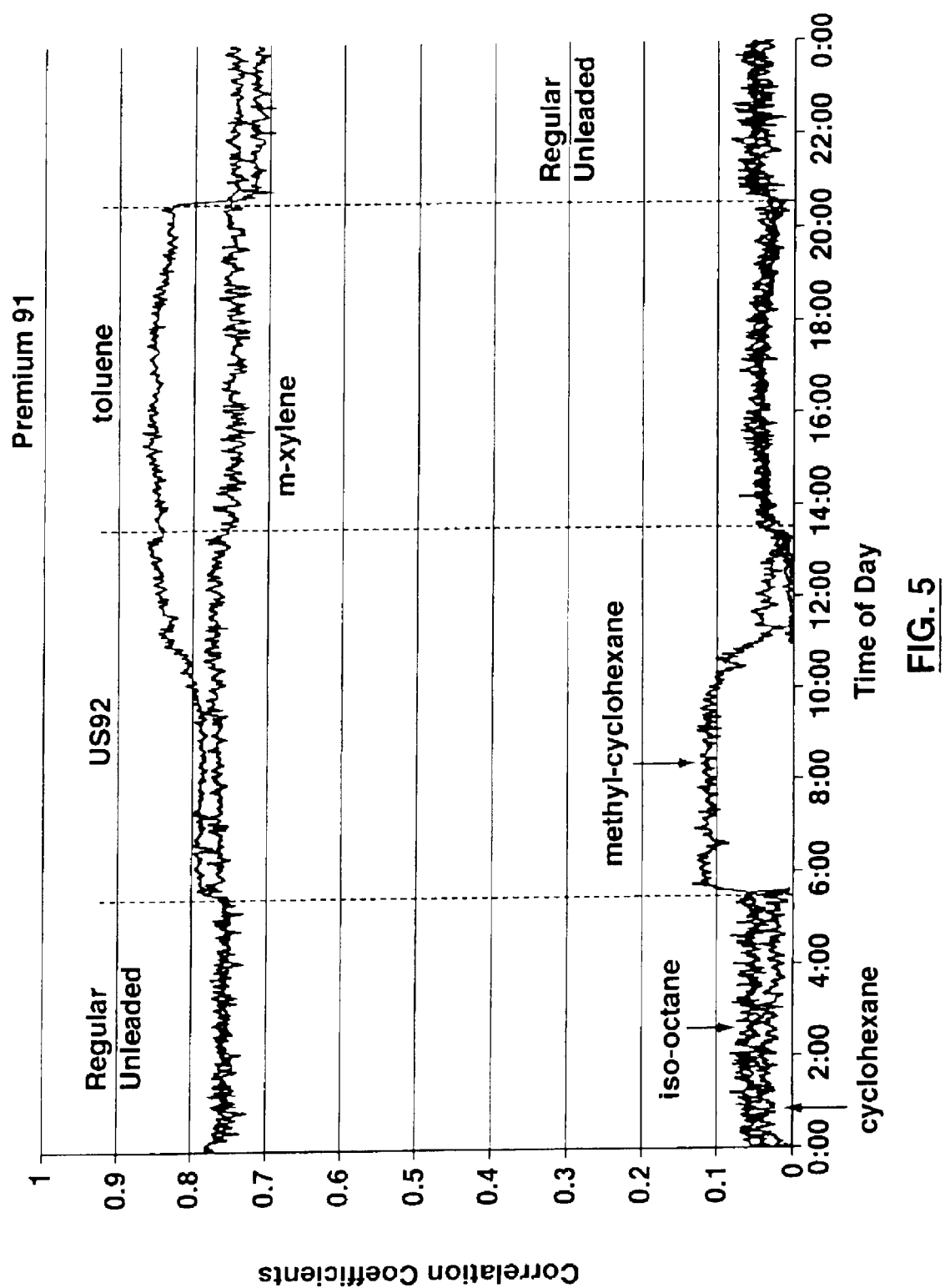
FIG. 5 illustrates a graph of measured optimized correlation coefficients for five incoming pure compounds over a finite time period during the day.
Figure 6:
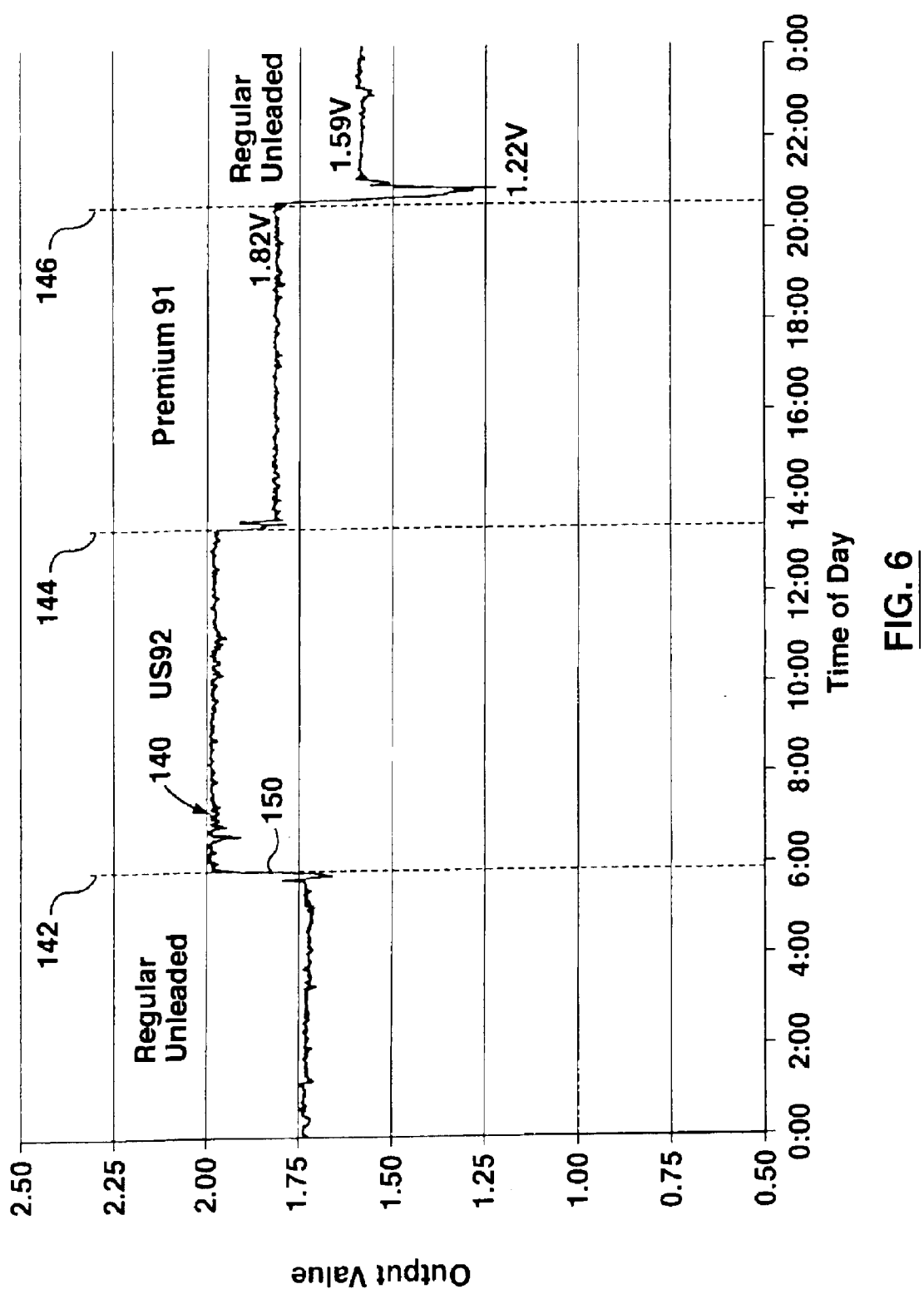
FIG. 6 illustrates a graph of measured output voltage corresponding to transition interfaces between three grades of gasoline over a finite time period during the day.

Three product interfaces occurred in a 24-hour period. As illustrated in FIG. 5, no single correlation coefficient responded reliably at every product interface. Furthermore, the magnitude of the changes at some interfaces were small relative to the degree of scatter, giving an unsatisfactory signal to noise ratio. These problems are overcome by calculating a single output value by using equations [2a, 2b and 3] in accordance with the present invention. As previously described, the output value is derived from the correlation coefficients of the pure compound reference spectra, and the correlation coefficient of the current (incoming) spectrum to a stored spectrum of the product which had been flowing in the previous few minutes. FIG. 6 shows this calculated output (in real or near real-time) value plotted as function gasoline flow over a period of 24-hours. The output value, defined by 140, reliably detects gasoline interfaces, as indicated at 142, 144, 146, and gives a good signal to noise ratio. For example, the interface, indicated by 142, between regular unleaded and US 92 is defined by a relatively well defined voltage step, as indicated at 150.

A further advantage of this method for detecting gasoline interfaces is that the algorithm was designed to exaggerate the difference in output values right at the interface. This is useful in cases where two different grades of gasoline have chemical compositions, which are very similar with respect to the compounds to which the Raman spectrometer is sensitive. A good example of this exaggerated change is seen in FIG. 6, where a transition at the interface, as indicated at 146, between premium 91 and regular unleaded occurs at approximately 20:30 hours. At the transition, the output value dips sharply from a value of 1.82 V to a minimum of 1.22 V, before rising again to level off at 1.59 V. The final values are related to the chemical composition of the product, while the size of the dip is related to the degree of difference between the incoming (current) product spectrum and the stored (previous) product spectrum. Two chemically similar gasoline products will give very similar final output values. However, the transition is still detected due to the small (but measurable) change in the product spectrum, which occurs at the interface.

Figure 7:
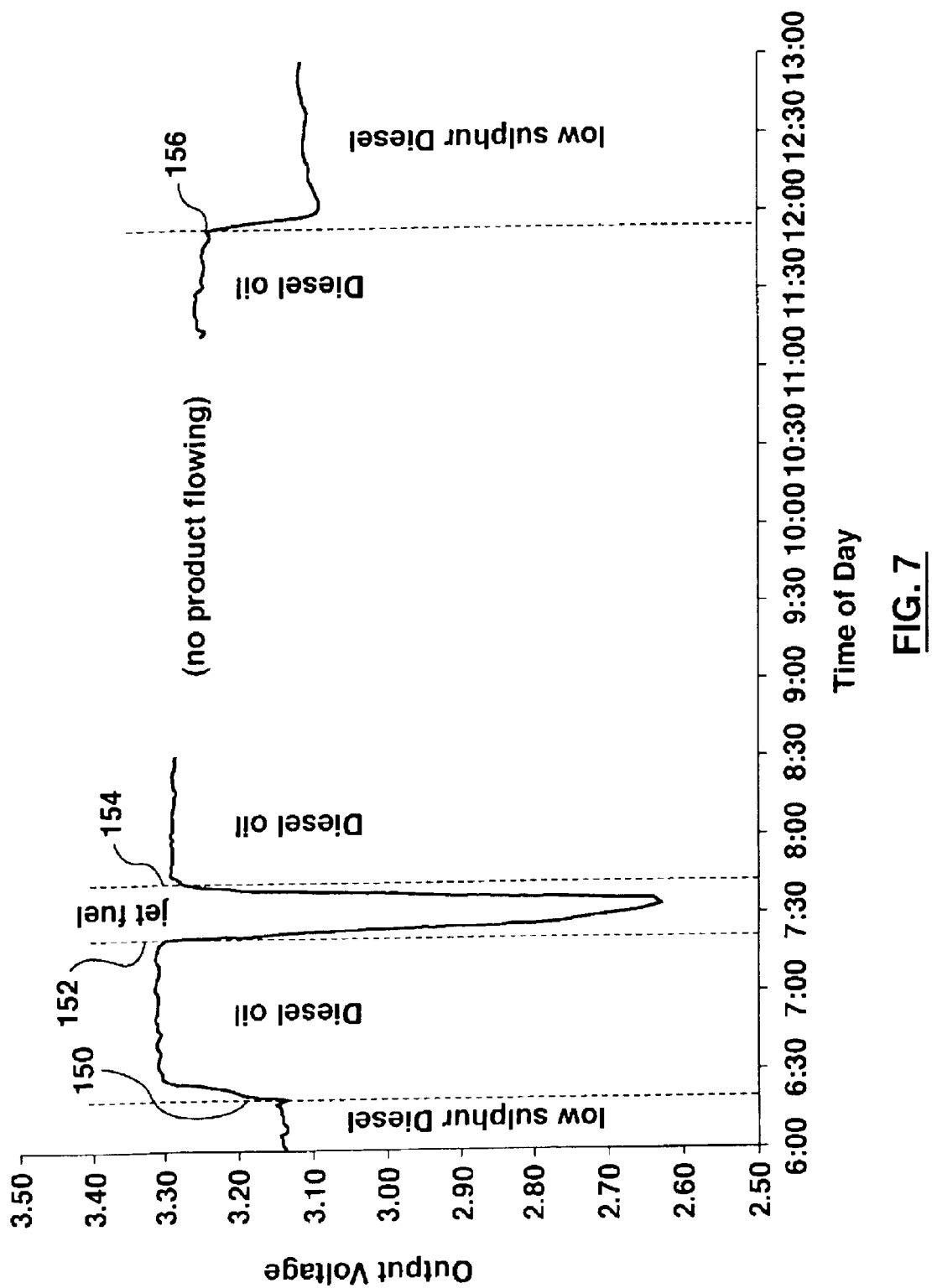
FIG. 7 illustrates a graph of measured output voltage corresponding to transition interfaces between low sulphur, diesel oil, and jet fuel over a finite time period during the day.

As described in the flow chart of FIG. 2, a different strategy (fluorescence signal strength) is used to detect product interfaces between the distillates. This successfully differentiates between jet fuel, diesel oil, low sulphur diesel, and furnace oil (not shown) as illustrated in the first field trail results shown in FIG. 7. FIG. 7 provides a plot of output voltage, which is calculated using equation [1], against time of day. FIG. 7 shows a quick set of transitions from low sulphur diesel to diesel oil, as indicated at 150, diesel oil to jet fuel, as indicated at 152, followed by a return to diesel oil, indicated at 154, then back to low sulphur diesel, as indicated at 156. No product was flowing through the pipeline between 08:35 and 11:15 hours. Particularly noteworthy among this set of transitions are the clear differences between diesel oil and low sulphur diesel, as these products can be difficult to distinguish by previously existing technologies. Transitions from a gasoline to a distillate or vice versa (not shown) are easily detected by this, and other, techniques.

Figure 8:
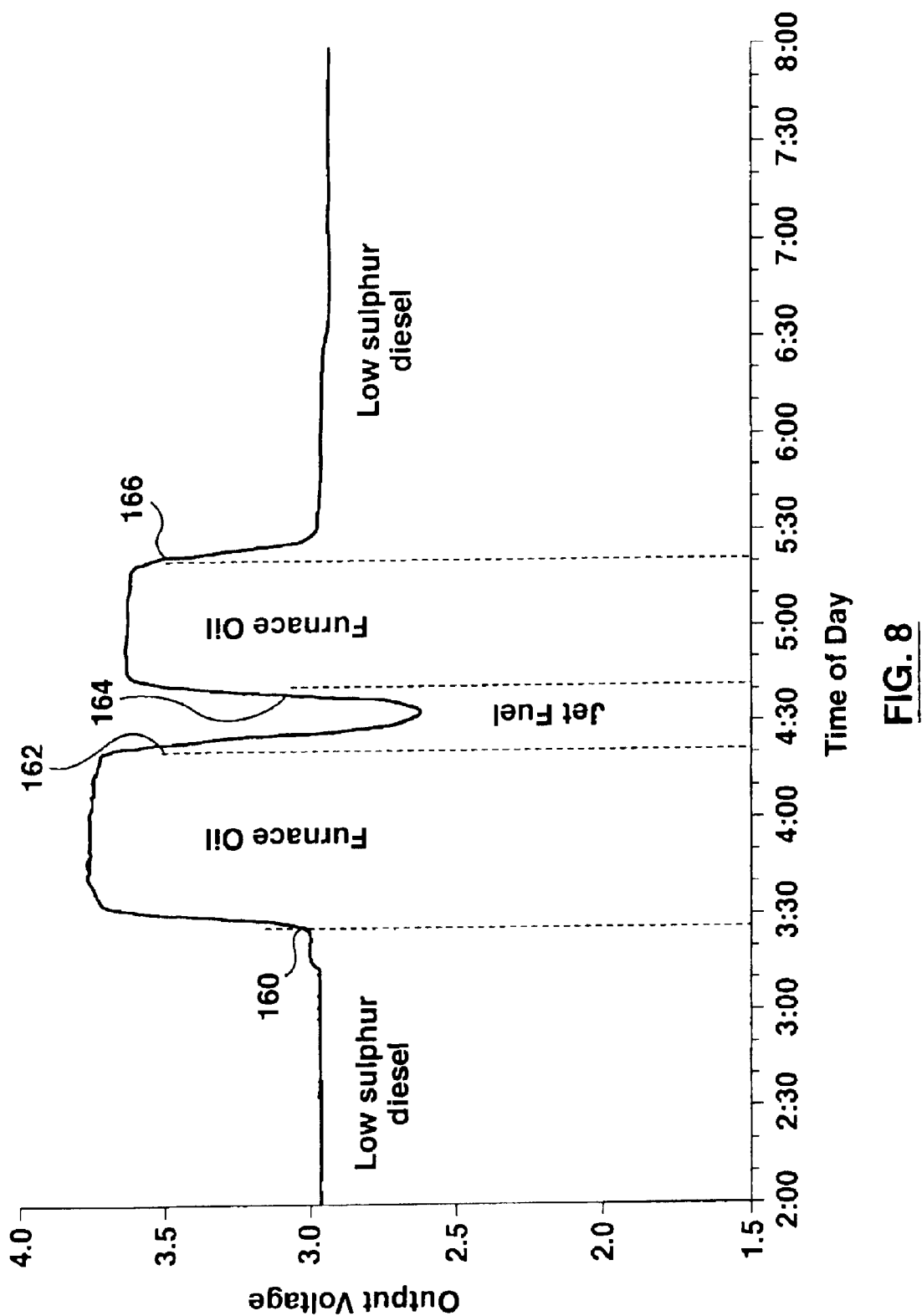
FIG. 8 illustrates a graph of measured output voltage corresponding to transition interfaces between low sulphur, furnace oil, and jet fuel over a finite time period during the day.

Data from a second field trial is shown in FIG. 8, wherein the interface transitions between jet fuel, low sulphur diesel oil, and furnace oil are shown. The transitions between low sulphur diesel oil and furnace oil, as indicated at 160, between furnace oil and jet fuel, indicated at 162, jet fuel and furnace oil, indicated at 164, and furnace oil and low sulphur diesel oil, indicated by 166, are clearly shown. Consequently, in accordance with the present invention, the Raman spectrometer system provides a clear indication of interfaces between petroleum products flowing in a pipeline. The system detects the interfaces between both various distillates and various grades of gasoline products by providing the end user or customer with a single indication value.

Obtaining good quality Raman data is a key ingredient for successfully detecting interfaces in a flowing product stream. The Raman spectra acquired by the Raman spectrometer system has excellent resolution and a good signal to noise ratio. The resolution of a Raman spectrum in general may be limited by the resolution (degree of monochromatically) of the excitation source, or by elements within the spectrometer. By using an external cavity to mode lock the diode laser, an excellent degree of monochromatically is achieved. If the excitation source is the limiting factor defining the resolution of the instrument, the observed excitation source linewidth (FWHM) of 0.2 nm will translate into a Raman shift of 4.5 cm$^{-1}$. The observed resolution of 7.2 cm$^{-1}$ (at the FWHM) is actually limited by the combined diffraction grating/focussing element inside the spectrometer, which has a dispersion of 1 mm/5 nm.

The high output power of the laser, high transmission through the single element spectrometer (low transmission losses) and low dark current level of the PMT detector all contributed to establishing a good signal to noise ratio. This means the scan time can be decreased to approximately 90 s. This sampling interval was short enough to detect product interfaces in real or near-real time. Ideally, the interface between products is sharply defined. In practice, some mixing occurs in the pipeline, depending on the level of activity (product flow rates) through the line. Real interfaces can thus span a period of up to 9 minutes, a time significantly greater than the sampling period.

The spectrometer as designed is compact and rugged, ideal for in-situ use in hostile environments. In this application, the spectrometer unit was located outdoors, adjacent to the gasoline pipeline. The sampling method is non-invasive and non-destructive (i.e. not a drop of product was consumed in the testing). This feature is also attractive for situations in which contamination may be an issue, for example in the two extreme cases in which the sample is either designed for human consumption or is highly toxic.

Comparing the incoming (current) product spectrum with a stored spectrum of product, which had been flowing a few minutes previously, proved to be the most sensitive method for detecting gasoline to gasoline product interfaces. The algorithm was designed to produce an exaggerated difference in output values right at an interface, then stabilize over a period of a few minutes to an output value related to the bulk chemical composition of the current product. This feature is invaluable for distinguishing between gasoline of very similar compositions.

The software in general was designed to be robust. Distinguishing between gasoline on the basis of correlation, rather than fit coefficients eliminates "noise" due to changes in the Raman signal intensity. The software was also designed to compensate for small gradual or sudden changes in the position (channel number) of the major Raman. The software corrects for this by "tracking" the toluene ring breathing mode, which has a Raman shift of 1001 cm$^{-1}$. In the region scanned, this peak always appears as the strongest feature in the Raman spectra of gasoline. The software routine finds this peak in the incoming product spectrum and compares its position with that of the analogous feature in the stored reference spectrum of toluene. If the position (1001 cm$^{-1}$) of the toluene peak (incoming spectrum) shifts, the shift is corrected so that the maximum of the toluene peak in the incoming spectrum occurs at the same channel number (1001 cm$^{-1}$) as in the reference spectrum. The fitting routines are then performed as normal on the corrected (shifted) incoming data. Such shifts could arise from a change in the behavior of the scanner motor, a sudden shift (mode hop) in the excitation wavelength, or a gradual shift in the excitation wavelength due to temperature induced changes in the alignment of the external cavity.

In accordance with the present invention, the Raman spectrometer system described herein, is not limited to specifically detecting interfaces between petroleum products. The system and product differentiation algorithm can be utilized to detect product interfaces in a variety of gas or liquid products, by means of accordingly varying the excitation source wavelength and other wavelength dependent components (e.g. gratings) in the system.

We claim:

1. A system for spectroscopically differentiating fluid flowing in a conduit, the system comprising:
   a light source for producing light suitable for Raman spectroscopy;
   a sample cell mounted adjacent the conduit, the sample cell having a first opening, through which fluid diverted from the conduit enters the sample cell, and a second opening, through which fluid returned to the conduit exits the sample cell, the sample cell having portions allowing light from the light source to impinge on the fluid contained therein;
   a Raman spectrometer for receiving the light scattered from the fluid, the Raman spectrometer is mounted with the sample cell adjacent the conduit, and the Raman spectrometer generating an optical signal corresponding to the scattered light;
   an optical detection device for converting the optical signal to an electronic signal; and
   a computer device for processing the electronic signal to differentiate the fluid flowing in the conduit.

2. The system of claim 1, wherein the light source and optical device are mounted with the sample cell adjacent the conduit.

3. The system according to claim 2, wherein the sample cell, light source, Raman spectrometer, and optical device are housed in an explosion proof box, the explosion proof box mounted adjacent to the conduit.

4. The system of claim 2, wherein the light source includes a diode laser.

5. The system of claim 4, further comprising at least one mirror placed outside the sample cell to increase the number of times that the light impinges on the fluid.

6. The system of claim 5, wherein the optical detection device is a photomultiplier tube.

7. A system for spectroscopically differentiating fluid flowing in a conduit, the system comprising:
   a light source capable of operating in more than one mode for producing light suitable for Raman spectroscopy;
   an external cavity device for locking a single mode of the light source;
   a sample cell having a first opening, through which fluid diverted from the conduit enters the sample cell, and a second opening, through which fluid returned to the conduit exits the sample cell, the sample cell having portions allowing light from the mode-locked light source to impinge on the fluid contained therein;
   a Raman spectrometer for receiving the light scattered from the fluid, the Raman spectrometer generating an optical signal corresponding to the scattered light;
   an optical detection device for converting the optical signal to an electronic signal; and
   a computer device for processing the signal to differentiate the fluid flowing in the conduit.

8. The system of claim 7, wherein the light source includes a diode laser.

9. The system of claim 8, wherein the external cavity device provides frequency-selective optical feedback for locking the single mode.

10. The system of claim 9, wherein the diode laser and the external cavity device cooperate to form a mode-locked external cavity laser that emits substantially monochromatic light with a spectral resolution of about 0.2 nm.

11. The system of claim 10, further comprising mirrors placed outside the sample cell to increase the number of times that the light impinges on the fluid.

12. The system of claim 11, wherein the optical detection device is a photomultiplier tube.

13. The system of claim 12, wherein the system is installed in-situ on a working conduit.

14. A system for spectroscopically differentiating fluid flowing in a conduit, the system comprising:
   a light source for producing light suitable for Raman spectroscopy;
   a sample cell having a first opening, through which fluid diverted from the conduit enters the sample cell, and a second opening, through which fluid returned to the conduit exits the sample cell, the sample cell having portions allowing light from the light source to impinge on the fluid contained therein;
   a Raman spectrometer for receiving the light scattered from the fluid, the Raman spectrometer generating a Raman spectrum corresponding to the scattered light;
   a computer device for determining whether the fluid is gasoline by comparing the Raman spectrum to a reference set of spectra, each member of the set of spectra corresponding to a compound characteristic of gasoline; and
   a fluorescence detector, for measuring the fluorescence of the fluid, wherein if the computer device determines that the fluid is not gasoline, an output value is provided that is a function of the fluorescence and that is indicative of the identity of the fluid, and if the computer device determines that the fluid is gasoline, the computer device performs a further analysis on the fluid to gain information about the identity thereof.

15. The system of claim 14 wherein if the computer device determines that the fluid is gasoline, the computer device compares the Raman spectrum to a previous Raman spectrum of the fluid in the conduit obtained a predetermined amount of time prior to the generation thereof, thereby determining if the fluid that yielded the Raman spectrum is substantially the same as the fluid that yielded the previous Raman spectrum.

16. The system of claim 15, wherein if the computer device determines that the fluid is gasoline, the computer device calculates an output value, V, which provides information about the identity of the fluid, the output value given by $$V = C_{M,previous} + 1.0 + 5(1 - R_{pp}) \text{ if } C_{M,new} - C_{M,previous} \geq 0 \text{ and } R_{pp} > R_{thresh}$$

$$V = C_{M,previous} + 1.0 - 5(1 - R_{pp}) \text{ if } C_{M,new} - C_{M,previous} < 0 \text{ and } R_{pp} > R_{thresh}$$

$$V = C_{M,new} + 1.0 + 5(1 - R_{pp}) \text{ if } C_{M,new} - C_{M,previous} \geq 0 \text{ and } R_{pp} \leq R_{thresh}$$

$$V = C_{M,new} + 1.0 - 5(1 - R_{pp}) \text{ if } C_{M,new} - C_{M,previous} < 0 \text{ and } R_{pp} \leq R_{thresh}$$

where $R_{PP}$ is a correlation coefficient between the Raman spectrum and the previous spectrum, $R_{thresh}$ is a pre-defined cut-off, $C_{M,new}$ is a moving constant that is computed from the Raman spectrum and $C_{M,previous}$ is a moving constant that is computed from the previous Raman spectrum.

17. The system of claim 16, wherein the light source includes a diode laser.

18. The system of claim 17, wherein the external cavity device provides frequency-selective optical feedback for locking a single mode of the diode laser.

19. The system of claim 18, wherein the diode laser and the external cavity device cooperate to form a mode-locked external cavity laser that emits substantially monochromatic light with a spectral resolution of about 0.2 nm.

20. The system of claim 19, further comprising at least one mirror placed outside the sample cell to increase the number of times that the light impinges on the fluid.

21. The system of claim 20, wherein the optical detection device is a photomultiplier tube.

22. The system of claim 20, wherein the system is installed in-situ on a working conduit.

23. A method for spectroscopically differentiating fluid flowing in a conduit, the method comprising
  diverting fluid from the conduit to a sample cell mounted adjacent the conduit;
  producing light with a light source suitable for Raman spectroscopy;
  allowing light from the light source to impinge on the fluid contained in the sample cell;
  providing a Raman spectrometer for receiving the light scattered from the fluid, the Raman spectrometer mounted with the sample cell adjacent the conduit;
  the Raman spectrometer generating a signal corresponding to the scattered light; and
  processing the signal to differentiate the fluid flowing in the conduit.

24. The method of claim 23, wherein the light source and optical device are mounted with the sample cell adjacent the conduit.

25. The method of claim 24, wherein, in the step for producing light, the light source includes a diode laser.

26. The method of claim 25, further comprising placing at least one mirror outside the sample cell to increase the number of times that the light impinges on the fluid.

27. A method for spectroscopically differentiating fluid flowing in a conduit, the method comprising:
  diverting fluid from the conduit to a sample cell;
  producing light suitable for Raman spectroscopy with a light source capable of operating in more than one mode;
  locking a single mode of the light source;
  allowing light from the mode-locked light source to impinge on the fluid contained in the sample cell;
  providing a Raman spectrometer for receiving the light scattered from the fluid;
  the Raman spectrometer generating a signal corresponding to the scattered light; and
  processing the signal to differentiate the fluid flowing in the conduit.

28. The method of claim 27, wherein, in the step of producing light, the light source includes a diode laser.

29. The method of claim 28, wherein, in the step of locking a single mode, an external cavity device provides frequency-selective optical feedback.

30. The method of claim 29, wherein, in the step of locking a single mode, the diode laser and the external cavity device cooperate to form a mode-locked external cavity laser that emits substantially monochromatic light with a spectral resolution of about 0.2 nm.

31. The method of claim 30, further comprising placing at least one mirror outside the sample cell to increase the number of times that the light impinges on the fluid.

32. The method of claim 31, further comprising installing the system in-situ on a working conduit.

33. A method for spectroscopically differentiating fluid flowing in a conduit, the system comprising:
  diverting fluid from the conduit to a sample cell;
  producing light with a light source suitable for Raman spectroscopy;
  allowing light from the light source to impinge on the fluid contained in the sample cell;
  providing a Raman spectrometer for receiving the light scattered from the fluid;
  the Raman spectrometer generating a Raman spectrum corresponding to the scattered light;
  determining whether the fluid is gasoline by comparing the Raman spectrum to a reference set of spectra, each member of the set of spectra corresponding to a compound characteristic of gasoline;
  measuring the fluorescence of the fluid;
  if the fluid is not gasoline, calculating an output value that is a function of the fluorescence and that is indicative of the identity of the fluid; and
  if the fluid is gasoline, performing further analyses on the fluid to gain information about the identity thereof.

34. The method of claim 33, wherein the step of performing further analyses includes:
  comparing the Raman spectrum to a previous Raman spectrum of the fluid in the conduit obtained a predetermined amount of time prior to the generation thereof; and
  determining if the fluid that yielded the Raman spectrum is substantially the same as the fluid that yielded the previous Raman spectrum.

35. The method of claim 34, wherein the step of performing further analyses includes:
  calculating an output value, V, which provides information about the identity of the fluid, the output value given by $V = C_{M,previous} + 1.0 + 5(1 - R_{pp})$ if $C_{M,new} - C_{M,previous} \geq 0$ and $R_{pp} > R_{thresh}$ $V = C_{M,previous} + 1.0 - 5(1 - R_{pp})$ if $C_{M,new} - C_{M,previous} < 0$ and $R_{pp} > R_{thresh}$ $V = C_{M,new} + 1.0 + 5(1 - R_{pp})$ if $C_{M,new} - C_{M,previous} \geq 0$ and $R_{pp} \leq R_{thresh}$ $V = C_{M,new} + 1.0 - 5(1 - R_{pp})$ if $C_{M,new} - C_{M,previous} < 0$ and $R_{pp} \leq R_{thresh}$ where $R_{PP}$ is a correlation coefficient between the Raman spectrum and the previous spectrum, $R_{thresh}$ is a pre-defined cut-off, $C_{M,new}$ is a moving constant that is computed from the Raman spectrum and $C_{M,previous}$ is a moving constant that is computed from the previous Raman spectrum.

36. The method of claim 35, wherein, in the step of producing light, the light source includes a diode laser.

37. The method of claim 36, wherein, in the step of locking a single mode, an external cavity device provides frequency-selective optical feedback.

38. The method of claim 37, wherein, in the step of locking a single mode, the diode laser and the external cavity device cooperate to form a mode-locked external cavity laser that emits substantially monochromatic light with a spectral resolution of about 0.2 nm.

39. The method of claim 38, further comprising placing at least one mirror outside the sample cell to increase the number of times that the light impinges on the fluid.

40. The method of claim 39, further comprising installing the system in-situ on a working conduit.

41. The method of claim 33, wherein, in the step of determining, the compound includes at least one of mono-substituted benzene, meta-substituted benzene, tri-substituted benzene, para-substituted benzene, branched alkanes and cyclic alkanes.

\* \* \* \* \*

UNITED STATES PATENT AND TRADEMARK OFFICE
CERTIFICATE OF CORRECTION

PATENT NO. : 6,734,963 B2
DATED : May 11, 2004
INVENTOR(S) : Heather A. Gamble et al.

It is certified that error appears in the above-identified patent and that said Letters Patent is hereby corrected as shown below:

Column 1,
Line 18, "laser" should read -- lasers --;

Column 3,
Line 3, "interface" should read -- inderfaces --;

Column 5,
Line 34, "PMI" should read -- PMT --;
Line 50, "sealed" should read -- scaled --;

Column 6,
Line 23, "Iso-octane" should read -- iso-octane --;
Line 26, "1001 cm$^1$" should read -- 1001 cm$^{-1}$ --.

Column 8,
Line 31, "fits" should read -- fit --.

Column 10,
Line 13, "loss" should read -- less --;
Line 23, "iso octane" should read -- iso-octane --.

Signed and Sealed this

Nineteenth Day of April, 2005

JON W. DUDAS
*Director of the United States Patent and Trademark Office*